United States Patent
Purich

(10) Patent No.: US 11,744,878 B2
(45) Date of Patent: Sep. 5, 2023

(54) METHODS FOR TREATMENT OF COVID-19 SYNDROME

(71) Applicant: ChiRhoClin, Inc., Burtonsville, MD (US)

(72) Inventor: Edward D. Purich, Silver Spring, MD (US)

(73) Assignee: CHIRHOCLIN, INC., Burtonsville, MD (US)

( * ) Notice: Subject to any disclaimer, the term of this patent is extended or adjusted under 35 U.S.C. 154(b) by 229 days.

(21) Appl. No.: 17/389,571

(22) Filed: Jul. 30, 2021

(65) Prior Publication Data
US 2022/0054592 A1    Feb. 24, 2022

Related U.S. Application Data

(60) Provisional application No. 63/067,492, filed on Aug. 19, 2020.

(51) Int. Cl.
*A61K 38/22*    (2006.01)
*A61K 9/00*    (2006.01)

(52) U.S. Cl.
CPC ........ *A61K 38/2235* (2013.01); *A61K 9/0019* (2013.01)

(58) Field of Classification Search
CPC .... A61K 38/2235; A61P 11/00; C07K 14/645
See application file for complete search history.

(56) References Cited

U.S. PATENT DOCUMENTS

| | | | |
|---|---|---|---|
| 4,246,374 A | 1/1981 | Kopchik | |
| 4,278,751 A | 7/1981 | Specht et al. | |
| 4,366,228 A | 12/1982 | Specht et al. | |
| 4,491,628 A | 1/1985 | Ito et al. | |
| 4,548,891 A | 10/1985 | Riediker et al. | |
| 4,585,876 A | 4/1986 | Fischer et al. | |
| 4,681,959 A | 7/1987 | Ayen et al. | |
| 5,019,482 A | 5/1991 | Ai et al. | |
| 5,049,628 A | 9/1991 | Nawata et al. | |
| 5,215,863 A | 6/1993 | Nawata et al. | |
| 5,492,793 A | 2/1996 | Breyta et al. | |
| 5,538,821 A | 7/1996 | Kakinuma et al. | |
| 5,545,702 A | 8/1996 | Oishi et al. | |
| 6,042,997 A | 3/2000 | Barclay et al. | |
| 6,284,185 B1 | 9/2001 | Tokuda et al. | |
| 6,294,239 B1 | 9/2001 | Tokuda et al. | |
| 6,524,708 B2 | 2/2003 | Puligadda et al. | |
| 6,602,646 B1 | 8/2003 | Sato et al. | |
| 6,730,452 B2 | 5/2004 | Brock et al. | |
| 7,282,324 B2 | 10/2007 | Weber et al. | |
| 7,358,027 B2 | 4/2008 | Ito et al. | |
| 7,359,108 B2 | 4/2008 | Hayes et al. | |
| 7,381,698 B2 | 6/2008 | Fein et al. | |
| 7,459,155 B2 | 12/2008 | Margolin et al. | |
| 7,479,364 B2 | 1/2009 | Ito | |
| 7,800,816 B2 | 9/2010 | Hayes et al. | |
| 7,813,030 B2 | 9/2010 | Lo et al. | |
| 7,947,285 B2 | 5/2011 | Fein et al. | |
| 2005/0002922 A1 | 1/2005 | Boismenu et al. | |
| 2005/0070472 A1 | 3/2005 | Gedulin et al. | |
| 2005/0129675 A1 | 6/2005 | Fein et al. | |
| 2006/0002912 A1 | 1/2006 | Fein et al. | |
| 2006/0019347 A1 | 1/2006 | Cho et al. | |
| 2007/0219222 A1 | 9/2007 | Moran et al. | |
| 2008/0146611 A1 | 6/2008 | Moran et al. | |
| 2009/0081184 A1 | 3/2009 | Margolin et al. | |
| 2009/0143377 A1 | 6/2009 | Ng et al. | |
| 2009/0192558 A1 | 7/2009 | Whitehurst et al. | |
| 2010/0048472 A1 | 2/2010 | Rosen et al. | |
| 2010/0197586 A1 | 8/2010 | Bevec et al. | |
| 2010/0204313 A1 | 8/2010 | Pasricha | |
| 2013/0323174 A1 | 12/2013 | Purich | |
| 2014/0349939 A1 | 11/2014 | Purich | |
| 2022/0362213 A1 | 11/2022 | Purich | |

FOREIGN PATENT DOCUMENTS

SU    624635 A    8/1978

OTHER PUBLICATIONS

Abstract of Russian Federation SU 624635, (Aug. 8, 1978).
Acute and Chronic Pancreatitis (enclosed pp. 1-16 available online Oct. 30, 2009, from http://web.archive.org/web/20091030012855/http://rezidentiat.3x.ro/eng/pancreatitaeng.htm).
Akisik et al.; "Dynamic Secretin-enhanced MR Cholangiopancreatography"; RadioGraphics, vol. 26, No. 3; May-Jun. 2006; pp. 665-677.
Boraschi et al.; "Pancreatic transplants: sectrin-stimulated MR pancreatography"; Abdominal Imaging, vol. 32; pp. 207-214 (Mar. 2007).
Branum et al.; "The use of pancreatic ductoscopy in the operative managment of benign and malignant pacreatic disorders"; Surg. Endo. (1995) 9: 53-55.
Callery et al.; "Prevention and Management of Pancreatic Fistula"; J. Gastrointest Surg., vol. 13; 2009; pp. 163-173.
Chey et al.; "Secretin Historical Perspective and Current Status"; Pancreas, vol. 43, No. 2; Mar. 2014; pp. 162-182.
Demirjian et al.; "The inconsistent nature of symptomatic pancreaticojejunostomy anastomotic structures"; HPB, vol. 12; 2010; pp. 482-487.
Fattahi et al. "Magnetic Resonance Imaging in Pancreas Transplantation"; Top Magn Reason Imaging, vol. 20, No. 1; pp. 49-55 (Feb. 2009).
Fukukura et al.; "Pancreatic Duct: Morphologic Evaluation with MR Cholangiopancreatography after Secretin Stimulation"; Radiology, vol. 222, No. 3; pp. 674-680 (Mar. 2002).

(Continued)

*Primary Examiner* — Jeffrey E. Russel
(74) *Attorney, Agent, or Firm* — CANTOR COLBURN LLP

(57) ABSTRACT

The invention relates generally to methods for treating and modulating the severity of COVID-19 syndrome. The methods comprise administering a therapeutically effective amount of a pharmaceutical composition to a human patient, the composition comprising secretin and a pharmaceutically acceptable carrier.

13 Claims, No Drawings

(56) References Cited

OTHER PUBLICATIONS

Gibril et al.; "Metastatic Gastrinomas: Localization with Selective Arterial Injection of Secretin"; Radiology vol. 198; pp. 77-84 (Jan. 1996).

Gillams et al.; "Diagnosis of Duct Disruption and Assesment of Pancreatic Leak with Dynamic Stimulated MR Cholangiopancreatography"; AJR, vol. 186; pp. 499-506 (Feb. 2006).

Gillams et al.; "Diagnosis of Duct Disruption and Assessment of Pancreatic Leak with Dymanic Secretin-Stimulated MR Cholangiopancreatography"; AJR (2006), 186:449-506.

Guy et al.; "Protein Content of Precipitates Present in Pancreatic Juice of Alcoholic Subjects and Patients with Chronic Calcifying Pancreatitis"; Gastroenterology; vol. 84; Jan. 1983; pp. 102-107.

Heverhagen et al.; "Pancreatic Transplants: Noninvasive Evaluation with Secretin-augmented MR PAncreatography and MR Perfusion Measurements—Preliminary Results"; Radiology, vol. 233, No. 1; pp. 273-280 (Oct. 2004).

Imamura et al.; "Use of Selective Arterial Secretin Injection Test to Guide Surgery in Patients with Zollinger-Ellison Syndrome"; World Journal of Surgery, vol. 17 No. 4; pp. 433-438 (Jul./Aug. 1993).

International Preliminary Report on Patentability and Written Opinion of the International Searching Authority for International Patent Application No. PCT/US2013/025820; dated Aug. 19, 2014; 6 Pages.

International Search Report for International Patent Application No. PCT/US2013/025820 International Filing Date: Feb. 13, 2013; dated Apr. 23, 2013; 2 Pages.

Kiem et al.; "Failure of Secretin to Prevent or Ameliorate Cerulein-induced Pancreatitis in the Rat"; Hepatogastroenterology; vol. 32; 1985; pp. 91-96.

Kuiper et al.; "Diagnostic Efficacy of the Secretin Stimulation Test for the Zollinger-Ellison Syndrome: an Intra-Individual Comparison Using Different Dosages in Patients and Controls"; Pancreatology; vol. 10; 2010; pp. 14-18.

Lankisch et al.; "Influence of Secretin on the Course of Acute Experimental Pancreatis in Rats"; Digestion; vol. 26; 1983; pp. 187-191.

M. R. Goulden, The pain of chronic pancreatities: a persisten clinical challenge, The British Pain Society; British Journal of Pain, vol. 1, No. 1, 2013, pp. 8-22.

Madsen et al.; "The intraductal Pancreatic Pressure in Chronic Obstructive Pancreatitis"; Scand. J. Gastroenterol.; vol. 17; 1982; pp. 553-554.

Mass of an Adult, from https://hypertextbook.com/facts/2003/AlexSchlessingerman.shtml, pp. 1-4, accessed Aug. 6, 2017.

Matos et al.; "Pancreatic Duct: Morphologic and Functional Evaluation with Dynamic MR Pancreatography after Secretin Stimulation"; Radiology, vol. 203, pp. 435-441 (May 1997).

Monril et al.; "Pancreatic Duct After Pancreatoduodenectomy: Morphologic and Functional Evaluation with Secretin-Stimulated MR Pancreatography"; AJR, vol. 183, pp. 1267-1274 (Nov. 2004).

Noda et al.; "Bromhexine Hydrochloride Eliminates Protein Plugs and Relieves Attacks of Pancreatitis"; Pancreas; col. 15, No. 2; 1997; pp. 209-2011.

Renner et al.; "Protective Effects of Exogenous Secretin on Ceruletide-induced Acute Pancreatitis in the Rat"; J. Clin. Invest.; vol. 72; Sep. 1983; pp. 1081-1092.

SecreFlo (Secretin) (from http://www.rxlist.com/secreflo-drug/clinical-pharmacology.htm, enclosed pp. 1-3), (2016).

Shinohara et al.; "A case of mucin-producing bile duct tumor which responded to bromhexine hydrochloride treatment and radiotherapy"; Tando; vol. 7; 1993; pp. 527-534.

Spanos et al.; "Bile leaks from the duct of Luschka (subvesical duct): a review"; Langenbecks Arch Surg (2006) 391:441-447.

Tsujimoto et al.; "Effect of Bromhexine Hydrochloride Therapy for Alcholic Chronic Pancreatitis"; Alcohol. Clin. Exp. Res.; vol. 29, No. 12; Dec. 2005; pp. 272S-276S.

Tympner et al., "The Treatment of Chronic Recurrent Pancreatitis with Depot Secretin—a Preliminary Report" Hepato-gastroenterol, 33, (1986), pp. 159-162.

Tympner et al.; "Viscosity and Trypsin Activity of Pure Pancreatic Juice in Chronic Pancreatitis"; Acta Hepatogastroenterol.; vol. 25; 1978; pp. 73-76.

Yamaguchi et al., "Litmus Paper Helps Detect Potential Pancreatoenterostomy Leakage", The American Journal of Surgery, vol. 175, Mar. 1998, 2 pages.

Yamamoto et al.; "Double Doses of Secretin Contribute to Diagnosis of Zollinger-Ellison Syndrome in Secretin adn Selective Arterial Secretion Injection Tests—a Case Report"; Digestive Dis. and Sci.; vol. 50 No. 11; Nov. 2005; pp. 2034-2036.

METHODS FOR TREATMENT OF COVID-19 SYNDROME

CROSS-REFERENCE TO RELATED APPLICATIONS

This Application claims priority to U.S. Provisional Patent Application Ser. No. 63/067,492 filed Aug. 19, 2020, which is incorporated by reference herein in its entirety.

BACKGROUND OF THE INVENTION

1. Field of the Invention

The invention relates generally to methods for treating COVID-19 syndrome, and more specifically to methods of preventing or modulating the severity of COVID-19 syndrome and its symptoms in a human patient by administering a therapeutically effective amount of a pharmaceutical composition comprising secretin and a pharmaceutically acceptable carrier.

2. Brief Description of the Related Art

COVID-19 syndrome displays some similarities to acute pancreatitis, specifically in regards to the inflammatory response "Systemic Inflammatory Response Syndrome, SIRS" they induce. In fact, SIRS is the most serious patient symptoms for acute pancreatitis and it results in hospital intensive care and is the main cause of death. Acute pancreatitis starts as an inflammation of the pancreas that occurs when digestive enzymes leak out of the acinar cells in the pancreas begin damaging the pancreas. The etiology of acute pancreatitis in humans is unknown, while the etiology of COVID-19 syndrome is the virus invasion of human cells through the Angiotensin Converting Enzyme "ACE 2" receptors on the cell surface. For the COVID-19 virus the ACE-2 receptors on Alveolar Type 2 cells in the lungs of humans. The virus attaches to the ACE-2 receptors and inserts itself into the cell and forces the cell to make more viral particles. The trauma results in destruction of the Alveolar Type 2 cell and the release of viral particles to infect more alveolar Type 2 cells. The destruction of the Alveolar Type 2 cells induces a severe inflammatory response in the lungs. ACE-2 receptors are present in many tissues of human body. In fact, the gastrointestinal tract or 'GI Tract", contains more than 100 fold greater concentration of ACE-2 receptors. COVID-19 infection of the GI Tract appears to occur in only 38 percent of the patients as compared to 58% in lungs. The much lower viral infection of GI Tract may well be associated with its ability to remove irritants by vomiting, diarrhea and even by the digestion process.

COVID-19 syndrome displays some of the same symptoms and conditions as acute pancreatitis, including symptoms of SIRS. It is known that in some people with COVID-19, the immune system releases immune messengers, called cytokines, into the bloodstream out of proportion to the threat or long after the virus is no longer a threat. In some cases, a cytokine storm may result, which is an overreaction of the body's immune system similar to SIRS. When this happens, the immune system attacks the body's own tissues, potentially causing significant harm. A cytokine storm triggers an exaggerated inflammatory response that may damage the heart. brain, liver, pancreas, blood vessels, kidneys, and lungs, and increase formation of blood clots throughout the body, similar to acute pancreatitis.

Secretin is a member of the vasoactive intestinal peptide (VIP) family of peptides and binds to VIP receptors throughout the human body ex. brain, lung, eyes, and most organs of the body. In humans, secretin binds to a receptor in the brain to trigger pancreatic ductal cell stimulation to initiate pancreatic fluid flow in the pancreas. It also binds to VIP receptors in the brain and other tissues of the body.

RLF-100 (aviptadil) is a vasoactive intestinal peptide that has demonstrated rapid recovery from respiratory failure in the most critically ill patients with COVID-19. At the same time, independent researchers have reported that aviptadil blocked replication of the SARS coronavirus in human lung cells and monocytes. On the surface of the Type II alveolar cells is found a high concentration of VIP receptors. One can hypothesize that RLF-100 may be interfering with SARS-CoV-2 virus by populating these VIP receptors on the surface of Type II alveolar cells and sterically and/or allosterically interfere with SARS-CoV-2 virus from binding to the angiotensin converting enzyme 2 (ACE-2) receptors that are also on the surface.

There are currently no vaccines or reliable treatment for COVID-19 syndrome. Accordingly, more effective treatment methods that prevent or modulate the severity of COVID-19 in human patients is needed. The present invention is believed to be an answer to these needs.

SUMMARY OF THE INVENTION

In one aspect, the present invention is directed to a method of preventing or modulating the severity of COVID-19 syndrome in a human patient, comprising the step of administering to a patient suffering from COVID-19 virus infection, a therapeutically effective amount of a pharmaceutical composition comprising secretin and a pharmaceutically acceptable carrier.

This and other aspects will become apparent upon reading the following detailed description of the invention.

DETAILED DESCRIPTION OF THE INVENTION

As indicated above, RLF-100 (aviptadil) is a vasoactive intestinal peptide (VIP) that has demonstrated rapid recovery from respiratory failure in the most critically ill patients with COVID-19, and it has been reported that aviptadil blocked replication of the SARS coronavirus in human lung cells and monocytes. On the surface of the Type II alveolar cells is a high concentration of VIP receptors. While not wishing to be bound by any particular theory, it may be theorized that RLF-100 could be interfering with SARS-CoV-2 virus by populating these VIP receptors on the surface of Type II alveolar cells and preventing SARS-CoV-2 virus from binding the ACE-2 receptors. As secretin can bind to VIP receptors as well, secretin may have a similar action on the SARS-CoV-2 virus. Secretin is highly and rapidly distributed in the body and even rapidly crosses the blood-brain barrier, thus making it a good therapeutic compound for treatment of COVID-19 syndrome. Secretin, currently a FDA approve drug that is safe and effective for use in evaluation of pancreas function is being evaluated for possible treatment in acute pancreatitis during active patient episodes of systematic inflammatory response syndrome (SIRS) and which is similar to symptoms presented by infection with SARS-CoV-2 virus in humans.

Thus, the present invention is directed to a method of preventing or modulating the severity of COVID-19 syndrome in a human patient, comprising the step of administering to a patient suffering from COVID-19 viral infection a therapeutically effective amount of a pharmaceutical composition comprising secretin and a pharmaceutically acceptable carrier.

Secretin is a 3055.5 MW (27 amino acid) gastrointestinal peptide hormone originally extracted from the porcine duodenum. The primary action of secretin is to increase the volume and bicarbonate content of pancreatic juice (Gutierrez L V, et al., Gut 13:721-25 (1972); Laugier R, et al., Digestion 54:54-60 (1993); Cavallini G, et al., Dig. Dis. Sci. 37(1):93-96 (1992)). It also increases the pancreatic duct diameter (Glaser J, et al., Int. J. Pancreatol. 15:195-200 (1994); Tulassay Z, et al., Gastroenterol. J. 51:47-50 (1991)) and causes sphincter of Oddi relaxation (Geenen J E et al., Gastroenterology 78:317-24 (1980); Laugier R. Endoscopy 26:222-27 (1994)). Recently, a new synthetic porcine secretin has been developed that has been shown to be equally effective as a pancreatic secretagogue. In the methods of the invention, secretin may be used from any source. Preferably the secretin used in the methods of the present invention is the naturally occurring form, the synthetic form, or the genetically recombined form of porcine, bovine or human secretin. More preferably the secretin is synthetic porcine secretin or synthetic human secretin. One useful form of porcine secretin is manufactured by ChiRhoClin, Inc. (Burtonsville, Md.) and was sold under the trade name "SECREFLO" by Repligen Corporation (Waltham, Mass.). Another useful form of porcine secretin is manufactured by ChiRhoClin, Inc. (Burtonsville, Md.) with the tradename "porcine secretin". A useful form of human secretin is manufactured and sold by ChiRhoClin, Inc. under the tradename "ChiRhoStim®".

The secretin may be combined with a pharmaceutically acceptable carrier to form a pharmaceutical composition. Thus, the pharmaceutical compositions of this invention comprise secretin from any source outlined above (including pharmaceutically acceptable salts thereof) in combination with any pharmaceutically acceptable carrier, adjuvant or vehicle. Pharmaceutically acceptable carriers, adjuvants and vehicles that may be used in the pharmaceutical compositions of the present invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered by any route that produces acceptable bioavailability. Suitable administration methods include, but are not limited to, parenteral methods such as intravenous (e.g, IV Bolus over 1 minute), subcutaneous and intramuscular and per os (by mouth), or sublingual, and transdermal bolus or continuous infusions of secretin may be used. Secretin would be administered as soon after diagnosis of COVID-19 syndrome as possible and given daily (in divided doses or continuous infusion) for about 3 days to about 14 days.

The secretin compounds of the invention are preferably administered internally, e.g., intravenously, in the form of conventional pharmaceutical preparations, for example in conventional enteral or parenteral pharmaceutically acceptable excipients containing organic and/or inorganic inert carriers, such as water, gelatin, lactose, starch, magnesium stearate, talc, plant oils, gums, alcohol, Vaseline, or the like. The pharmaceutical preparations can be in conventional solid forms, for example, tablets, dragées, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

The pharmaceutical preparation of the invention should include an amount of secretin effective for preventing COVID-19 viral infection. The effective dosage will depend on several factors, including body weight, body mass index, age, gender and disease severity. Suitable dosages may be, for example, in the range of about 16 to 100 micrograms secretin, or about 64 to 192 36 micrograms secretin, or about 128 to 500 micrograms secretin per dose. In addition, multiple doses of secretin may be required to be administered each day over a period of time (for example, a dose of 16 micrograms secretin (approximately 0.2 micrograms per kilogram body weight) intravenously, four times per day for 7 days.

In one embodiment, the dosage of secretin may be administered intravenously as a function of body weight. Useful ranges for this route of administration include, for example, 0.2 mcg secretin/kg body weight two times per day (daily dose=0.4 mcg/kg); 0.4 mcg secretin/kg body weight four times per day (daily dose=1.6 mcg/kg); or 0.8 mcg secretin/kg body weight four times per day (daily dose=3.2 mcg/kg).

EXAMPLES

The invention is further described by the following Examples, but is not intended to be limited by the Examples. All parts and percentages are by weight and all temperatures are in degrees Celsius unless explicitly stated otherwise.

Dosing and Administration

Synthetic human secretin is preferably administered to a human patient through an intravenous line. ChiRhoStim® (synthetic human secretin for injection) is reconstituted according to the package insert. The contents of each vial (16 mcg) is reconstituted with 8 mL of sterile physiologic saline (0.9%) USP. A test dose of 0.2 mcg (0.1 mL) will be given initially to the patient and if no allergic reaction is noted in one minute, the remainder of the total dose is given over 3 minutes.

All patients with COVID-19 will have standard of care treatment which includes: 1) intravenous fluids, 2) analgesics and 3) laboratory studies. In addition to standard care, patients will be treated with escalating doses of intravenous synthetic human secretin. One possible dosage regimen is as follows:

Day 1: 0.2 mcg/kg ChiRhoStim® two times a day (daily dose=0.4 mcg/kg)

Day 2: 0.4 mcg/kg ChiRhoStim® four times a day (daily dose=1.6 mcg/kg)

Day 3: 0.8 mcg/kg ChiRhoStim® four times a day (daily dose=3.2 mcg/kg)

Patients will be monitored for 14 days or until discharge, whichever comes first.

Patient Evaluation

The change in biochemical parameters that represent local and systemic effects of COVID-19 syndrome will be monitored throughout secretin administration for patients for changes from baseline values of C-reactive protein, pancreatic enzymes, sedimentation rate, hematocrit, APACHE II score, and oxygen saturation. Continuous monitoring of vital signs per standard of care and adverse events should also be monitored. Respiratory issues are a cardinal symptom of COVID-19 syndrome and such symptoms will be monitored and treated based on standard practice guidelines. Vital signs will be recorded at baseline prior to administration of study medication (synthetic human secretin) and continuously throughout the study period per standard of care.

Patients with COVID-19 syndrome treated with secretin would be expected to experience rapid clearing of viral particles accompanied by an improvement in blood oxygen and a decrease in laboratory markers associated with COVID-19 inflammation. It is believed that secretin (a vasoactive intestinal peptide) competitively inhibits binding of SARS-CoV-2 virus to ACE-2 receptors by binding to nearby VIP receptors thus interfering with replication of the SARS-CoV-2 virus in human lung cells and immune cells (monocytes) to affect a treatment for COVID-19 syndrome.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. A method of preventing or modulating the severity of COVID-19 syndrome in a human patient, comprising the step of administering to a patient suffering from SARS-CoV-2 virus infection a therapeutically effective amount of a pharmaceutical composition comprising secretin and a pharmaceutically acceptable carrier.

2. The method of claim 1, wherein said secretin is a naturally occurring form of secretin.

3. The method of claim 1, wherein said secretin is a synthetic form of secretin.

4. The method of claim 3, wherein said synthetic form of secretin is synthetic human secretin.

5. The method of claim 1, wherein said secretin is a genetically recombined form of porcine, bovine, or human secretin.

6. The method of claim 1, wherein the amount of secretin administered to said patient in said pharmaceutical composition ranges from 16 to 100 micrograms per day.

7. The method of claim 1, wherein the amount of secretin administered to said patient in said pharmaceutical composition ranges from 64 to 192 micrograms per day.

8. The method of claim 1, wherein the amount of secretin administered to said patient in said pharmaceutical composition ranges from 128 to 500 micrograms per day.

9. The method of claim 1, wherein the amount of secretin administered to said patient in said pharmaceutical composition is about 0.2 mcg secretin/kg bodyweight of said patient and is administered twice per day (daily dose=0.4 mcg/kg).

10. The method of claim 1, wherein the amount of secretin administered to said patient in said pharmaceutical composition is about 0.4 mcg secretin/kg bodyweight of said patient and is administered four times per day (daily dose=1.6 mcg/kg).

11. The method of claim 1, wherein the amount of secretin administered to said patient in said pharmaceutical composition is about 0.8 mcg secretin/kg bodyweight of said patient and is administered four times per day (daily dose=3.2 mcg/kg).

12. The method of claim 1, wherein said pharmaceutically acceptable carrier is selected from the group consisting of ion exchangers, alumina, aluminum stearate, lecithin, serum proteins, human serum albumin, buffer substances, phosphates, glycine, sorbic acid, potassium sorbate, partial glyceride mixtures of saturated vegetable fatty acids, water, salts or electrolytes, protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat, and combinations thereof.

13. The method of claim 1, wherein said pharmaceutical composition is administered intravenously.

\* \* \* \* \*